United States Patent [19]

Patel

[11] Patent Number: 4,544,756

[45] Date of Patent: Oct. 1, 1985

[54] ZWITERIONIC 2-ALKYL IMIDAZOLINES AS EMULSIFYING AGENTS FOR OIL BASED DRILLING FLUIDS

[75] Inventor: Arvind D. Patel, Houston, Tex.

[73] Assignee: Dresser Industries, Inc., Dallas, Tex.

[21] Appl. No.: 552,641

[22] Filed: Nov. 17, 1983

[51] Int. Cl.$^4$ .......................................... C07D 233/18
[52] U.S. Cl. .................................................. 548/354
[58] Field of Search ........................................ 548/354

[56] References Cited

U.S. PATENT DOCUMENTS

| | | | |
|---|---|---|---|
| Re. 23,227 | 5/1950 | Blair et al. ........................... | 252/8.55 |
| 2,713,582 | 7/1955 | Smith .................................. | 548/352 |
| 3,728,277 | 4/1973 | Foley ................................. | 252/309 |
| 3,849,435 | 11/1974 | Diery et al. .......................... | 548/354 |
| 4,109,094 | 8/1978 | Trivedi et al. ................... | 548/354 X |
| 4,374,737 | 2/1983 | Larson et al. ..................... | 252/8.5 P |

FOREIGN PATENT DOCUMENTS 1294385  5/1969  Fed. Rep. of Germany ...... 548/354

*Primary Examiner*—Richard A. Schwartz
*Attorney, Agent, or Firm*—Richard M. Byron

[57] ABSTRACT

Improved emulsifying agents for oil based drilling fluids, compared to imidazoline materials presently being used in oil based drilling fluids, that not only are excellent emulsifiers for oil based drilling fluids, but also are effective wetting agents and fluid loss control agents in invert (water-in-oil) systems, are obtained from imidazolines prepared by reacting long chain fatty acids with polyalkylene polyamines to form a 2-alkyl imidazoline, and then reacting the 2-alkyl imidazoline with an activated dicarboxylic acid to form the desired 2-alkyl imidazoline derivative.

7 Claims, No Drawings

ZWITERIONIC 2-ALKYL IMIDAZOLINES AS EMULSIFYING AGENTS FOR OIL BASED DRILLING FLUIDS

BACKGROUND OF THE INVENTION

A variety of emulsifying agents including imidazolines have been proposed and used in oil based drilling fluids. In U.S. Pat. No. 4,374,737, a drilling fluid composition is disclosed containing diethanolamide, a fatty acid, an imidazoline/amide mixture and a non-polluting oil. Stable water-in-oil emulsions that are proposed for use in oil well drillmuds are described in U.S. Pat. No. 3,728,277 as an admixture comprising (a) an imidazoline or oxazoline salt of a long chain fatty acid and (b) a salt of a long chain aliphatic amido amine and a long chain aliphatic carboxylic acid. U.S. pat. No. Re. 23,277 discloses a variety of imidazoline compounds that are said to inhibit the corrosion of metals in oil wells by corrosive oil or oil-brine mixtures. Included in the group of specific imidazolines disclosed are 2-oleylimidazoline and 1-oleoloxyethyl,2-ethylimidazoline. Derivaties of imidazoline and pyrimidine demulsifiers that are useful in breaking petroleum emulsions of the water-in-oil type obtained by the reaction between a polycarboxylic acid and highly oxypropylated substituted imidazolines and pyrimidines, are disclosed in U.S. Pat. No. 2,713,582.

SUMMARY OF THE INVENTION

Improved emulsifying agents for oil based drilling fluids, compared to imidazoline materials presently being used in oil based drilling fluids, that not only are excellent emulsifiers for oil based drilling fluids, but also are effective wetting agents and fluid loss control agents in invert (water-in-oil) systems, are obtained from 2-alkyl imidazolines prepared by reacting long chain fatty acids with polyalkylene polyamines to form 2-alkyl imidazolines, reacted with an activated dicarboxylic acid to form the 2-alkyl imidazoline derivatives.

DETAILED DESCRIPTION

The fatty acids used to make the imidazolines contain from about 12 to 22 carbon atoms and may be saturated or unsaturated, including, for example, lauric acid, myristic acid, palmitic acid, stearic acid, arachidic acid, behenic acid, dodecylinic acid, palmitoleic acid, oleic acid, ricinoleic acid, linoleic acid, linolenic acid, arachidonic acid, erucic acid and the like. Mixtures of acids may be used. Particularly useful are acid mixtures containing a major proportion of mono- or di-unsaturated fatty acids containing 16 to 18 carbon atoms. Commercial mixtures of acids such as tall oil and the like may be used satisfactorily.

The amines are polyalkylene polyamines and include diethylene triamine, triethylene tetramine, tetraethylene pentamine, and the like of the general formula $NH_2(CH_2CH_2NH)_nCH_2CH_2NH_2$ wherein n is 1 to 12, more preferably 1 to 4. For example, $NH_2(CH_2CH_2NH)_1 CH_2CH_2NH_2$, diethylene triamine.

The unsaturated dicarboxylic acids must contain at least one activated carbon-to-carbon olefinic double bond in an alpha-beta position in the molecule with respect to a carboxylic group, i.e., —C|C—COOH; and the dicarboxylic groups are preferably in a cisrelation to each other in the molecule. The acids preferably contain 4 to 6 carbon atoms. Typical activated carboxylic acids meeting these criteria include, maleic acid, itaconic acid, citraconic acid, aconitic acid, 3,4,5,6-tetrahydrophthalic acid, muconic acid, glutaconic acid, and the like; and anhydrides and alkyl monoesters thereof wherein the alkyl groups contain 1 to 8 carbon atoms. Preferably the acid form is used. Other alpha-beta unsaturated acids such as acrylic acid the trans form of maleic acid, fumaric acid, do not provide imidazoline products with the desired properties. While the reaction product of 3,4,5,6-tetrahydrophthalic acid with a 2-alkyl imidazoline has the desired structure and properties, the reaction product of 1,2,3,6-dihydrophthalic acid with the 2-alkyl imidazoline does not have the defined structure of this invention and characteristic —C=C—COOH group of the defined materials and is not useful or effective in the practice of this invention.

In the reaction to form the imidazoline, the molar ratio of amine to fatty acid will be varied from one mole of amine to about 0.5 to 2 moles of fatty acid. Good yields and products are obtained when the molar amount of fatty acid is greater than one mole per mole of amine to less than 2 moles per mole of amine. Better results are obtained with about 1.5 to 1.7 mole of fatty acid per mole of amine. Usually about 1.3 to about 1.8 moles of fatty acid per mole of amine result in satisfactory yields and product.

In the reaction of the imidazoline with the unsaturated dicarboxylic acids defined herein, a molar ratio of about one mole of imidazoline to about 0.2 to one or more mole(s) of dicarboxylic acid is used. The molar ratio more preferably is from one mole of imidazoline to about 0.4 to 0.8 mole of dicarboxylic acid on a cost/efficiency basis.

The emulsifying agents of this invention may be considered to be carboxylated imidazolines, Zwiterion 2-alkyl imidazolines or unsaturated cisdicarboxylic acid adducts of imidazolines. In any event, the emulsifying agents are prepared by first reacting a polyalkylene polyamine with a fatty acid to first form an amide which is then heated to a higher temperature to convert the diamide or aminoamide to a 2-alkyl imidazoline. This imidazoline is then reacted with cis-dicarboxylic acid having an activated carbon-to-carbon double bond to form a salt that rearranges to the emulsifying agent reaction product. This Zwiterionic 2-alkyl imidazoline is a mixture of two structures having the following general formulas when prepared from imidazolines of diethylene triamine and a long chain fatty acid and maleic acid.

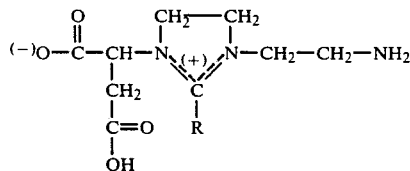

1-(2'-aminoethane)-2-alkayl-3-succinyl imidazole salt, and

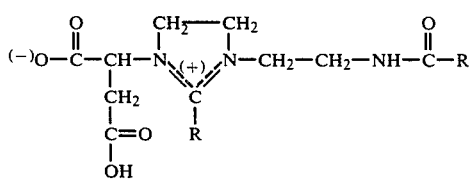

1-(2'-akylamido ethane)-2-alkyl-3-sucinyl imadzole salt wherein R is an unsaturated or saturated alkyl radical containing 12 to 22 carbon atoms. R is unsaturated $C_{18}$ alkyl groups when tall oil containing oleic and linoleic acids is used.

In the preparation of the 2-alkyl imidazoline derivatives, some variation in reaction conditions may be employed. In general, the polyalkylene polyamine is heated to about 70° C. to about 100° C. before the fatty acid is added so that the resulting salt or amide will be in a liquid state, and when about onehalf of the fatty acid has been added, the temperature of the rection mixture should be at about 100° C. to about 125° C. The fatty acid is added at such a rate that there is no substantial excess of unreacted acid present in the reaction mixture at any time. In other words, preferably the acid should be added at about its reaction rate with the polyalkylene polyamine. It is essential that the acid is added to the amine. To convert the the amine-fatty acid salts to the amide, usually the temperature of the reaction mixture is first raised to about 130° C. to 140° C. for one hour at reflux. Water is distilled off while keeping the temperature below about 150° C. To convert the amides to the desired 2-alkyl imidazolines, the reaction mixture temperature is normally increased to at least about 180° C., preferably above 180° C. to less than 300° C. for about 45 minutes to about one hour. The rate and extent of conversion of amides to the imidazolines is followed by collecting and measuring the water given off, there being one mole of water formed for each mole of imidazoline formed.

To obtain the dicarboxylic acid-imidazoline reaction products, the 2-alkyl imidazolines is brought to a temperature at a point above the melting point of the dicarboxylic acid to be used. A useful range is about 135° C. to about 160° C. The dicarboxylic acid is added slowly in powder form or in a melted state. While the reaction may be conducted at higher temperatures, a range of about 135° C. to 160° C. is preferred. This is normally obtained by controlling the rate of addition of the acid to imidazoline. After about one hour at this temperature, the reaction mix is heated to about 190° C. for one-half hour to one hour to finish off the reaction. The reaction mixture is then cooled to about 50° C. The dicarboxylic acid preferably is added at a rate, at above the melting point of the dicarboxylic acid, to control the reaction temperature to about 160° C. to 200° C.

The preparation and physical properties of the 2-alkyl imidazoline dicarboxylic acid adducts are described in the following Examples.

EXAMPLE I 25.75 grams of diethylenetriamine in 25 ml of xylene was added to a reaction vessel equipped with stirring, heating and condensor means, and heated to 80° C. 112.5 grams of distilled tall oil (43% linoleic acid, 44% oleic acid, 13% other $C_{12}$-$C_{22}$ fatty acids) was slowly added to the reaction vessel. When about one half of the acid had been added, the temperature of the reaction mixture was raised to 100°±10° C. and maintained at this temperature during the addition of the remainder of the acid. The mixture was then refluxed for 30 minutes at 135° C. At this point a water trap was connected and azeotropic water was distilled off up to 162° C. The amount of condensate collected was 8 ml. The mixture was then heated to 190° C. and maintained at this temperature for two hours while distilling off the xylene. An additional 3.3 ml of azeotropic water was collected. The mixture was then heated to 265° C. over a period of 30-40 minutes. During this time, an additional 3.5 ml of water azeotrope and 8 ml of xylene was collected. Infrared analysis of a sample taken from the reaction mixture confirmed the formation of the 2-alkyl imidazoline. This reaction mixture was cooled to 90° C., and 17.4 grams of fumaric acid was added to the reaction vessel. 10 ml of xylene was added and the mixture heated to reflux at 180° C. to 190° C. for one hour. The mixture was then cooled and 25 ml of heavy aromatic naphtha and 15 ml of methanol stirred in.

EXAMPLE II 25.75 grams of diethylenetriamine was reacted with 112.5 grams of distilled tall oil to obtain 2-alkyl imidazoline according to the procedure described in Example I. The reaction mixture was cooled to 150° C., and 17.4 grams of maleic acid was added. The reaction mixture was heated to 180° C. to 190° C. with 25 ml of heavy aromatic naphtha solvent. After one hour, the reaction mixture was cooled to 50° C. and 15 ml of methanol was stirred into the product.

EXAMPLE III 25.75 grams of diethylenetriamine was reacted with 112.5 grams of distilled tall oil to obtain 2-alkyl imidazoline according to the procedure described in Example I. The reaction mixture was cooled to 110° C., and 22.5 grams of 1,2,3,6-tetrahydrophthalic acid was added thereto. The reaction mixture was heated to 180° C. to 190° C. with 25 ml of heavy aromatic naphtha. After one hour, the reaction mixture was cooled to 50° C. and 15 ml of methanol stirred into the product.

To test the effectiveness of these materials in an emulsifier application, they were tested as oil base mud emulsifiers in accordance with procedures set forth in API Recommended Practice, API RP 13B Eighth Edition, April 1980, "STANDARD PROCEDURE for TESTING DRILLING FLUIDS". 12 pounds per gallon oil/brine (25% calcium chloride) formulations were prepared. The oil/brine ratios (O/B) are set forth in the table below. The samples were aged at 300° C. for 16 hours and tested at 115° C. Tests were conducted on both unaged and aged samples. The results obtained are set forth in Table I.

Tests of these formulations were conducted at 60/40 and 70/30 oil/brine ratios.

For the 60/40 O/B ratio, 142.73 grams of #2 diesel oil, 2.0 grams of lime, and 5 grams of organophilic clay were mixed for 20 minutes. 8 grams of reaction product and 151.04 grams of 25% calcium chloride solution were mixed in for 20 minutues. 192.54 grams of barite was stirred in and mixed for 20 minutes.

For the 70/30 ratio, oil mud formulation 165.76 grams of #2 diesel oil, 2.00 grams of lime, and 5 grams of organophilic clay were mixed for 20 minutes. 8.0 grams of reaction product and 112.76 grams of aqueous, 25% by weight, calcium chloride were added and mixed for 20 minutes. 206.50 grams of barite was slowly stirred into the mixture for 20 minutes.

TABLE I

| Example | Temperature | Oil/Brine Ratio | HT-HB F.L., ml. O/B Ratio |
| --- | --- | --- | --- |
| I | Initial | 60/40 | 0.5/2.6 |
|  | 300° F. | 60/40 | 3.0/2.8 |
|  | 300° F. | 70/30 | 14.7/9.5 |
| II | Initial | 60/40 | 1.8/1.2 |
|  | 300° F. | 60/40 | 1.6/1.4 |

TABLE I-continued

| Example | Temperature | Oil/Brine Ratio | HT-HB F.L., ml. O/B Ratio |
|---|---|---|---|
|  | 300° F. | 70/30 | 10.5/4.0 |
| III | 300° F. | 70/30 | 31.2/29.8 |

These data show the oil and brine fluid loss under the conditions of the test. Such loss is undesirable and minimum loss is desired. The maleic acid derivative of Example II shows much less fluid loss under varying conditions than the fumaric acid derivative of Example I; and a many-fold improvement over the 1,2,3,6-tetrahydrophtholic acid derivative of Example III, both of which are outside the scope of the present invention. When fluid loss is critical in oil field production methods, even a 0.1 to 1 additional ml loss shown by this test will represent substantial losses in large volume uses in the field.

For comparison purposes a commercial 2-alkyl imidazoline formulation prepared from diethylenetriamine and tall oil, was tested under similar conditions and total fluid loss was observed.

It is claimed:

1. Zwiterionic 2-alkyl imidazoline selected from the group consisting of

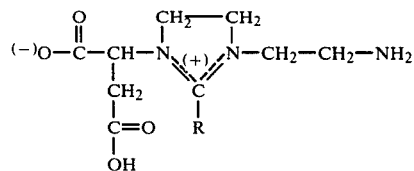

1-(2'-aminoethane)-2-alkyl-3-succinyl imidazole salt, and

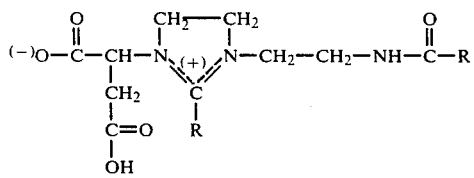

1-2'-akylamido ethane)-2-alkyl-3-succinyl imadzole salt; wherein R is an alkyl radical containing 12 to 22 carbon atoms.

2. An activated unsaturated dicarboxylic acid derivative of a 2-alkyl imidazoline prepared by first adding a long chain fatty acid containing 12 to 22 carbon atoms to a polyalkylene polyamine of the formula $NH_2(CH_2CH_2NH)_nCH_2CH_2NH_2$ wherein n is a number from 1 to 12, to form the 2-alkyl imidazoline, and reacting with said imidazoline reaction product an unsaturated dicarboxylic acid containing at least one activated carbon-to-carbon double bond in an alpha,beta position in the molecule with respect to a carboxylic acid group, —C‖C—COOH, said dicarboxylic acid containing 4 to 8 carbon atom, the carboxyl groups being in a cis relation to each other.

3. An activated unsaturated dicarboxylic acid derivative of a 2-alkyl imidazoline of claim 2 prepared by first adding the long chain fatty acid to the polyalkylene polyamine at a temperature of about 70° C. to about 100° C., and completing the reaction at a temperature in the range of greater than 180° C. to less than 300° C. for forming the 2-alkyl imidazoline, adding to said 2-alkyl imidazoline, the unsaturated dicarboxylic acid and reacting at a temperature of 135° C. to 200° C., said dicarboxylic acid containing 4 to 6 carbon atoms.

4. An activated unsaturated dicarboxylic acid derivative of a 2-alkyl imidazoline of claim 3 wherein the fatty acid contains a major proportion of fatty acids containing 16 to 18 carbon atoms, n is 1 to 4, and the unsaturated dicarboxylic acid is selected from the group consisting of maleic, itaconic, citraconic, aconitic, 3,4,5,6-tetrahydrophthalic, muconic and glutaconic acids.

5. An activated unsaturated dicarboxylic acid derivative of a 2-alkyl imidazoline of claim 4 wherein the fatty acids comprise a major proportion of oleic and linoleic acids, the polyalkylene polyamine is diethylenetriamine, and the unsaturated dicarboxylic acid is maleic acid.

6. An activated unsaturated dicarboxylic acid derivative of a 2-alkyl imidazoline of claim 5 wherein the molar ratio of diethylenetriamine to oleic and linoleic acids is one mole of diethylenetriamine to about 0.5 mole to about 2 moles of oleic and linoleic acids, and the molar ratio of 2-alkyl imidazoline reaction product to maleic acid is 1 to 0.2 to 1.

7. An activated unsaturated dicarboxylic acid derivative of a 2-alkyl imidazoline of claim 6 wherein the molar ratio of acid to amine is one to about 1.3 to 1.8, and the ratio of 2-alkyl imidazoline to maleic acid is 1 to 0.4 to 0.8.

* * * * *